United States Patent [19]

Kanzaki et al.

[11] Patent Number: 5,177,197
[45] Date of Patent: Jan. 5, 1993

[54] ISOLATED NUCLEOTIDE SEQUENCE EXPRESSING HUMAN TRANSFORMING GROWTH FACTOR-β1-BINDING PROTEIN

[75] Inventors: Tetsuto Kanzaki, Chiba, Japan; Anders Olofsson, Upsala, Sweden; Anita Morén, Upsala, Sweden; Christer Wernstedt, Upsala, Sweden; Ulf Hellman, Upsala, Sweden; Kohei Miyazono, Upsala, Sweden; Lena Claesson-Welsh, Upsala, Sweden; Carl-Henrik Heldin, Upsala, Sweden

[73] Assignee: Ludwig Institute for Cancer Research, New York, N.Y.

[21] Appl. No.: 487,343

[22] Filed: Feb. 27, 1990

[51] Int. Cl.$^5$ .................... C07H 15/12; C07H 17/00; A61K 37/24; C12P 21/06
[52] U.S. Cl. ................... 435/240.2; 536/23.5; 530/350; 530/399; 435/69.1; 435/240.2; 435/320.1
[58] Field of Search ............. 536/27, 28, 29; 530/350, 351, 387, 385, 395, 399; 435/240.2, 69.1, 320.1

[56] References Cited

PUBLICATIONS

Lee et al., (1988), Science, vol. 239: pp. 1288-1291.
Miyazono et al., Nature, 338: 158-160 (Mar. 9, 1989).
Miyazono et al., J. Biol. Chem., 263(13): 6407-6415 (1988).
Hynes, Cell, 48: 549-554 (1987).

Primary Examiner—David L. Lacey
Assistant Examiner—Gian P. Wang
Attorney, Agent, or Firm—Felfe & Lynch

[57] ABSTRACT

Purified protein known as platelet TGF-β1-BP (transforming growth factor-β1-binding protein) is described. The protein is useful for purposes such as the production of antisera which are useful in identifying complexes containing the binding protein, as well as in formation of labeled probes. Also described are purified DNA which expresses the protein, as well as messenger RNA translated into the protein. The protein contains 16 epidermal growth factors (EGF) like repeats, and 3 repeats not found in other proteins. The DNA for the protein is found to contain consensus sequences for hydroxylation of asparagine/aspartic acid residues, and, in the purified protein beta hydroxylated asparagine residues were found.

12 Claims, 16 Drawing Sheets

```
                                                    *                            *         M  D  T  K  L  M  C  L  L  F       10
TGAATTCGAAAGAGGTGGCTCTCTCTTTTCCCTCTTGTAATATTCTTTTCTTTTTTCTGTTTTTTAAACCTTCCAAGGCAAGTTCATGGATACTAAGCTGATGTGTTTGTTGTTC   120

F  F  S  L  P  P  L  L  V  S  N  H  T  G  R  I  K  V  V  F  T  P  S  I  C  K  V  T  C  T  K  G  S  C  Q  N  S  C  E  K    50
TTTTCTCCCTGCCTCCGCTCCTAGTGAGTAACCACACTGGCCGCATCAAGGTGGTCTTTACTCCGAGCCATCTGTAAAGTGACCTGCCACCAAGGGCAGCTGTCAGACAGCTGTGAGAAG  240

G  N  T  T  T  L  I  S  E  N  G  H  A  A  D  T  L  T  A  T  N  F  R  V  V  I  C  H  L  P  C  M  N  G  G  Q  C  S  S  R    90
GGGAACACCACCACTCTCATTAGTGAGAATGGTCATGCTGCCGACACCCTGACGGCCACGAACTTCCGAGTGGTAATTTGCCATCTTCCATGTATGAATGGTGGCCAGTGCAGTTCAAGG  360

D  K  C  Q  C  P  P  N  F  T  G  K  L  C  Q  I  P  V  H  G  A  S  V  P  K  L  Y  Q  H  S  Q  Q  P  G  K  A  L  G  T  H   130
GACAAATGTCAGTGCCCTCCAAATTTCACAGGAAAACTTTGTCAGATCCCAGTCCATGGTGCCAGGTGCCTAAACTTTATCAGCATTCCCAGCAGCCAGGCAAGGCGTTGGGGACGCAT   480

V  I  H  S  T  H  T  L  P  L  T  V  T  S  Q  Q  G  V  K  V  K  F  P  P  N  I  V  N  I  H  V  K  H  P  P  E  A  S  V  Q   170
GTCATCCATTCAACACATACCTTGCCTCTGACCGTGACTAGCCAGCAAGGAGTCAAAGTGAAATTTCCTCCTAACATAGTCAATATCCATGTGAAACATCCTCCTGAAGCTTCCGTCCAG  600

I  H  Q  V  S  R  I  D  G  P  T  G  Q  K  T  K  E  A  Q  P  G  Q  S  Q  V  S  Y  Q  G  L  P  V  Q  K  T  Q  T  I  H  S   210
ATACATCAGGTTTCAAGAATTGATGGCCCAACAGGCCAGAAGACAAAAGAAGCTCAACCAGGCCAATCCCAAGTCTGGTACCAAGGGCTTCCTGTCCAGAAGACCCAGACCATACATTCC  720

T  Y  S  H  Q  Q  V  I  P  H  V  Y  P  V  A  A  K  T  Q  L  G  R  C  F  Q  E  T  I  G  S  Q  C  G  K  A  L  P  G  L  S   250
ACATACTCCCACCAGCAGGTCATTCCTCACGTCTACCCGGTGGCTGCTAAGACACAGCTTGGCCGGTGCTTCCAGGAAACCATTGGGTCACAGTGTGGCAAAGCGCTCCCTGGCCTTTCA  840

K  Q  E  D  C  C  G  T  V  G  T  S  W  G  F  N  K  C  Q  K  C  P  K  K  P  S  Y  H  G  Y  N  Q  M  M  E  C  L  P  G  Y   290
AAGCAAGAGGACTGCTGTGGAACTGTGGGTACCTCCTGGGCTTTAACAAATGCCAGAAATGCCCAAGAAACCATCTTATCATGGATACAACCAAATGATGGAATGCCTACCGGGTTAT  960

K  R  V  N  N  T  F  C  Q  D  I  N  E  C  Q  L  Q  G  V  C  P  N  G  E  C  L  N  T  M  G  S  Y  R  C  T  C  K  I  G  F   330
AAGCGGGTTAACAACACCTTTTGCCAAGATATTAATGAATGTCAGCTACAAGGTGTATGCCCTAATGGTGAGTGTTTGAATACCATGGCAGCTATCGATGTACCTGCAAAATAGGATTT 1080

G  P  D  P  T  F  S  S  C  V  P  D  P  P  V  I  S  E  E  K  G  P  C  Y  R  L  V  S  S  G  R  Q  C  M  Y  P  L  S  V  H   370
GGCCCGGATCCTACCTTTTCAAGTTGTGTTCCTGATCCCCCTGTGATCTCGGAAGAGAAAGGGCCCGTTACCGACTTGTCAGTTCTGGAAGACAGTGTATGTACCCTCTGTCTGTTCAC 1320

L  T  K  Q  L  C  C  C  S  V  G  K  A  G  P  H  C  E  K  C  P  L  P  G  T  A  A  F  K  E  I  C  P  G  G  M  G  Y  T  V   410
CTCACCAAGCAGCTCTGCTGTTGTAGTGTGGGCAAGGCTGGGCCACACTGTGAGAAATGTCCCCTTCCAGGCACAGCTGCTTTTAAGGAAATCTGTCCTGGTGGAATGGGTTATACGGTT 1320
```

```
                                                                                                       M  D  T  K  L  M  C  L  L  F                                10
TGAATTCGAAAGAGTGGCTCTCCTTTCCCCTCTTGTATATTCTTTTCTGTTTTTTAAACCTTCAGGCAGTTCATGGATACTAAGCTAATGTGTTTGTGTTC                  120

F  F  S  L  P  P  L  L  V  S  N  H  T  G  R  I  K  V  V  F  T  P  S  I  C  K  V  T  C  T  K  G  S  C  Q  N  S  C  E  K                  50
TTTTTCCCTGCCTCGTCCCTCTAGTGATAACCACACTGGGCATCAAGGTGGTCTTTACTCCGAGCATCTGTAAAGTGACCTGTACAAAGGGCAGCTGTCAGAACAGCTGTGAGAAG    240

G  N  T  T  L  I  S  E  N  G  H  A  A  D  T  L  T  A  T  N  F  R  V  V  I  C  H  L  P  C  M  N  G  G  Q  C  S  S  R                     90
GGGAACACCACACTCATTAGTGAGAATGGTCATGCTGCGGACACCCTGACACCCACAAACTTCCGAGTGGTAATTTGCCATCTTCCATGTATGAATGGTGGCCAGTGCAGTTCAAGG   360

D  K  C  Q  C  P  P  N  F  T  G  K  L  C  Q  I  P  V  H  G  A  S  V  P  K  L  Y  Q  H  S  Q  Q  P  G  K  A  L  G  T  H                  130
GACAAATGTCAGTGCCCTCCAAATTTCACAGGAAAACTTTGTCAGATTCCAGTCCATGGTGCCAGTGTCCCAAGCTGTACCAGCACAGCCAGGGAAAGCGCTTGGGACGCAT       480

V  I  H  S  T  H  T  L  P  L  T  V  T  S  Q  Q  G  V  K  F  P  P  N  I  V  N  I  H  V  K  H  P  P  E  A  S  V  Q                       170
GTCATCCATTCAACACACACTTTGCCTCTGACCGTGACCAGCAGGAGTCAAGAGTCAAGTTCCCTCCTAACATAGTCAATATCCATGTGAAACATCCTCCAGAGCTTCGGTCCCAG   600

I  H  Q  V  S  R  I  D  G  P  T  G  Q  K  T  K  E  A  Q  P  G  Q  S  Q  V  S  Y  Q  G  L  P  V  Q  K  T  Q  T  I  H  S                  210
ATACATCAGGTTTCAAGAATTGATGGCCCAACAGGCCAGAAGACAAAGGAAGCTCAACCAGGCCAGAGCCAAGTCTCGTACCAGGGCTTGCCAGTACAGAAGACCCAGACCATACATTCC  720

T  Y  S  H  Q  Q  V  I  P  H  V  Y  P  V  A  A  K  T  Q  L  G  R  C  F  Q  E  T  I  G  S  Q  C  G  K  A  L  P  G  L  S                 250
ACATACTCCCACCAGCAGGTCATTCCCCACGTCTACCCGGTGGCCGCGAAGACACAGCTTGGCCGGTGCTTCCAAGAAACCATTGGTCAGCAGTGTGGCAAAGCCCTGCCTGGCTTTCA  840

K  Q  E  D  C  C  G  T  V  G  T  S  W  G  F  N  K  C  Q  K  C  P  K  K  P  S  Y  H  G  Y  N  Q  M  M  E  C  L  P  G  Y                 290
AAGCAAGAGGATTGCTGCGGGACTGTCGGTACCTCCTGGGGCTTTAACAAATGCCCAAGAAACCATCTATCATGGATACAACCAAATGATGGAATGCCTACCGGGTTAT          960

K  R  V  N  N  T  F  C  Q  D  I  N  E  C  Q  L  Q  G  V  C  P  N  G  E  C  L  N  T  M  G  S  Y  R  C  T  C  K  I  G  F                 330
AAGCGGGTTAACAACACCTTTTGCCAAGATATCAATGAATGCCAACTACAAGGGGTGTGCCCTAATGGAGAGTGTTTGAATACCATGGGCAGCTATCGATGCACCTGCAAAATAGGATTT  1080

G  P  D  P  T  F  S  S  C  V  P  D  D  P  P  V  I  S  E  E  K  G  P  C  Y  R  L  V  S  S  G  R  Q  C  M  Y  P  L  S  V  H             370
GGGCCGGATCCTACCTTCTCAAGTTGTGTGCCTGATGACCCCCCTGTGATCTCGGAAGAAAAAGGCCCCTGTTACCGACTGGTCAGTTCAGGTCGGCAGTGTATGTACCCTCTGTCTGTTCAC  1320

L  T  K  Q  L  C  C  C  S  V  G  K  A  G  P  H  C  E  K  C  P  L  P  G  T  A  A  F  K  E  I  C  P  G  G  M  G  Y  T  V               410
CTCACCAAGCAGCTCTGCTGTTGTAGTGTGGGCAAGGCTGGCCCCCACTGTGAGAAATGTCCCTTACCAGGAACAGCAGCCTTTAAGGAAATCTGTCCTGGTGGAATGGGTTATACGGTT    1320
```

FIG. 4b-1.

```
S G V H R R R P I H H H V G K G P V F V K P K N T Q P V A K S T H P P P L P A K      450
TCTGGGGTTCATAGACGCCAGGCCAATCCATCACCATGTAGGTAAAGGACCTGTATTTGTCAAGCCAAGAACACTCAACCTGCTAAAAGTACTCATCCTCCACTCTCCAGCCAAG      1440

E E P V E A L T F S R E H G A R S A E P E V A T A P P E K E I P S L D Q E K T K          490
GAAGAGCCAGTGGAGGCCCTGACTTCTCGGGAGCACGGGCCAGGAGTGCGACCAGAGTGCACTGCACCAGGGCCACTGCCAGAGTGCACAGCTGCACCCCCGAAAAGGAAATAACCTTCATTGATCAAGAGAAAACCAAA      1560

L E P G Q P Q L S P G I S A I H L H P Q F P V V I E K T S P P V P V E V A P P E A          530
CTTGAGCCTGGACAGCCTCAACCCCAGTCTCCAGGCATTTCGGCTATTCATCTGCATCCACAGTTTCCAGTAGTGATTGAAAAAACATCCTCGTCCCTGTGCCTGTGAGGTAGCTCCTCGAAGT      1680

S T S S A S Q V I A P T Q V T E I N E C T V N P D I C G A G H C I N L P V R Y T          570
TCTACAAGTTCTAGCCCAGTGTCCTCCTACTCAAGTCACAGTAGATTGCCTACTCAAGTCACAGAAATCAATGTACAGACCGTGGAGCCGGACATGTGAGACACTGGACCACTACCAGTGAGATACC      1800

C I C Y E G Y R F S E Q Q R K C V D I D E C T Q V Q H L C S Q G R C E N T E G S          610
TGATATATCTGTACGAGGGCTACAGGTTCAGTGAACAGCAGCGCAAGTGCGTGGACATAGATGAGTGTACCCAGGTCCAACACTCTGCTCCCAGGGCCGCTGTGAAAACACCGGAGGAAGT      1920

F L C I C P A G F M A S E E G T N C I D V D E C L R P D V C G E G H C V N T V G          650
TTCTGTGCATTGCCCAGCAGGATTTATGGCCAGTGAAGAGGGCACTAACTGCATAGATGTAGATGAATGTCTCCAGCCGGACGTCTGTGGGGAGGGGCACTGTGTGCAATACTGTGGGG      2040

A F R C E Y C D S G Y R M T Q R G R C E D I D E C L N P S T C P D E Q C V N S P          690
GCTTTCCGGTGTGAATACTGTGATAGCGGCTACAGGATGACCCAGCGGAGGCGGTGTGAGGACATTGACGAGTGTCTGAATCCCAGCACACTGCCCTGATGACCAGTGTGTGAATTCTCCT      2160

G S Y Q C V P C T E G F R G W N G Q C L D V D E C L E P N V C A N G D C S N L E          730
GGATCTTACCAGTGCGTTCCCTGCACAGAAGGATTCCGAGGCTGGAATGGACAGTGCCTTGATGTGGACGAGTGCCTCGAACCAAACGTCTGGCAAATGTGTAATGTCCAACCTTGAA      2280

G S Y M C S C H K G Y T R T P D H K H C R D I D E C Q Q G N L C V N G Q C K N T          770
GGCTCCTACATGTGTTCATGCCACAAGGGCTATACCCGGACTCCAGACCACAAGCACTGCAGAGATATTGATGAATGCCAGCAAGGAAATCTATGTAAAGTGGGCAGTGAAAATACC      2400

E G S F R C T C G Q Y Q L S A A K D Q C E D I D E C Q H R H L C A H G Q C R N          810
GAGGGCTCCTTCAGGTGCACCTGTGGACAGGGGTACAGCTGACTCCTAAGACCAGTGTGAAGATATCGATGAATGCCAGCACCGTCACCTCATCTGCCATGGCCAGTGCCGAGAAC      2520

T E G S F Q C V C D Q G Y R A S G L G D H C E D I N E C L E D K S V C Q R̄ḠD̄ C̄          850
ACTGAGGGCTCTTTCCAATGTGTGTGTGACCAGGGTTACAGAGCAATCGGGCCTTGGAGACCACTGTGAAGATATCAATGAATGCCTTGAAGACAAGAGTGTTTGCCAGAGAGGACACTGC      2640
```

FIG. 4b-2

```
I  N  T  A  G  S  Y  D  C  T  C  P  D  G  F  Q  L  D  D  N  K  T  C  Q  D  I  N  E  C  E  H  P  G  L  C  G  P  Q  G  E      890
ATTAATACTGCAGGGTCCTATGATTGTACTTGTCCTGATGGTTTCCAGCTAGATGACAATAAAACATGTCAAGATATTAATGAATGTGAACATCCAGGGCTCTGTGGTCCGCAAGGGGAG    2760

C  L  N  T  E  G  S  F  H  C  V  C  Q  Q  G  F  I  S  A  D  G  R  T  C  E  D  I  D  E  C  V  N  N  T  V  C  D  S  H         930
TGCCTAAACACAGAGGGTTCTTTCCATTGTGTCTGCCAGCAGGGTTTCATATCTGCAGATGGCCGAACTTGTGAAGATATTGATGAATGTGTAAACAACACTGTTTGTGACAGTCAC    2880

G  F  C  D  N  T  A  G  S  F  R  C  L  C  Y  Q  G  F  Q  A  P  Q  D  G  Q  G  C  V  D  V  N  E  C  L  L  S  G  V  C         970
GGGTTTTGTGACAATACAGCTGGCTCCTTCCGCTGCCTCTGTTATCAGGGCTTTCAACCCCCACAGGATGGGCAAGGGTGTGTGGATGTGAATGAATGTCTACTGAGTGGGGTGTGT    3000

G  E  A  F  C  E  N  V  E  G  S  F  L  C  V  C  A  D  E  N  Q  E  Y  S  P  M  T  G  Q  C  R  S  R  T  S  T  D  L  D  V    1010
GGTGAAGCCTTCTGTGAAAACGTGGAAGGGTCCTTCCTGTGTGTGTGTGCTGATGAAAATCAAGAGTACAGCCCCATGACTGGGCAGTGCCGCTCCAGACTTCCACAGATTTAGATGTA 3120

A  G  W  G  D  N  C  E  I  F  P  C  P  V  L  G  T  A  E  F  T  E  M  C  P  K  G  K  G  F  V  P  A  G  E  S  S  E  A       1090
GCCGGATGGGGAGATAACTGCGAAATCTTCCCCTGCCCTGTCCTGGGAACTGCTGAGTTCACTGAAATGTGCCCAAAGGGAAAGGGTTTTGTGCCTGCTGGAGAATCATCTGAAGCT    3360

G  G  E  N  Y  K  D  A  D  E  C  L  L  F  G  Q  E  I  C  K  N  G  F  C  L  N  T  R  P  G  Y  E  C  Y  C  K  Q  G  T  Y    1130
GGTGGTGAACTATAAAGATGCAGATGAATGCCTACTTTTTGGACAAGAAATCTGCAAAAATGGTTTCTGTTTGAACACTCGGCCTGGGTATGAATGCTACTGTAAGCAAGGAACGTAC 3480

Y  D  P  V  K  L  Q  C  F  D  M  D  E  -  C  Q  D  P  S  S  C  I  D  G  Q  C  V  N  T  E  G  S  Y  N  C  F  C  T  H  P  M  1170
TATGATCCTGTGAAACTGCAGTGCTTTGATATGGATGAATGCCAAGACCCCAGTAGTTGTATAGATGGCCAGTGTGTTAATACAGAGGGCTCTTACAACTGCTTCTGTACACCCCATG 3600

V  L  D  A  S  E  K  R  C  I  R  P  A  E  S  N  E  Q  I  E  E  T  D  V  Y  Q  D  L  C  W  E  H  L  S  D  E  Y  V  C  S    1210
GTCCTGGATGCGTCAGAAAAAAGATGTATACGACCCGCTGAGTCAAACAAATGAGCAAATTGAGGAAACTGATGTCTACCAAGATCTCTGTTGGGAACATCTGAGTGATGAATACGTGTGTAGC 3720

R  P  L  V  G  K  Q  T  T  Y  T  E  C  C  C  L  Y  G  E  A  W  G  M  Q  C  A  L  C  P  L  K  D  S  D  D  Y  A  Q  L  C    1250
CGGCCTCTTGTGGGCAAGCAGACAACAGTACACGGAATGTTGCTGCCTCTATGGAGAGGCCTGGGGCATGCAGTGCCTCTGCCCCTTGAAGGATTCAGATGACTATGCTCAGCTGTGT 3840

N  I  P  V  T  G  R  R  Q  P  Y  G  R  D  A  L  V  D  F  S  E  Q  Y  T  P  E  A  D  P  Y  F  I  Q  D  R  F  L  N  S  F    1290
AACATCCCGGTGACGGGACGGCGCCAGCCATATGGACGGGACGCCCTTGTTGACTTCAGTGAACAGTATACTCCAGAAGCCGATCCCTACTTCATCCAAGACCGTTTCTAAATACCTTT 3960
```

| repeat no. | | | | amino acid no. |
|---|---|---|---|---|
| 1 | DINEC | QLQGVC PNGECLNTMGSYRCT CKIGFGPDPTFSS | CV | 300- 340 |
| 2 | EINEC | TVNPDIC GAGHCINLPVRYTCI CYEGYRFSEQQRK | CV | 546- 587 |
| 3 | DIDEC | TQVQHLC SQGRCENTEGSFLCI CPAGFMASEEGTN | CI | 588- 629 |
| 4 | DVDEC | LRPDVC GEGHCVNTVGAFRCEYCDSGYRMTQRGR | CE | 630- 670 |
| 5 | DIDEC | LNPSTC PDEQCVNSPGSYQCVPCTEGFRGWNGQ | CL | 671- 710 |
| 6 | DVDEC | LEPNVC ANGDCSNLEGSYMCS CHKGYTRTPDHKH | CR | 711- 751 |
| 7 | DIDEC | QQGNLC VNGQCKNTEGSFRCT CGQGYQLSAAKDQ | CE | 752- 792 |
| 8 | DIDEC | QHRHLC AHGQCRNTEGSFQCV CDQGYRASGLGDH | CE | 793- 833 |
| 9 | DINEC | LEDKSVC QRGDCINTAGSYDCT CPDGFQLDDNKT | CQ | 834- 874 |
| 10 | DINEC | EHPGLCGPQGECLNTEGSFHCV CQQGFSISADGRT | CE | 875- 916 |
| 11 | DIDEC | VNNTVCDSHGFCDNTAGSFRCL CYQGFQAPQDGQG | CV | 917- 958 |
| 12 | DVNEC | ELLSGVC GEAFCENVEGSFLCV CADENQEYSPMTGQCR | CF | 959-1001 |
| 13 | DADEC | LLFGQEIC KNGFCLNTRPGYECY CKQGTYYDPVKLQ | CF | 1097-1139 |
| 14 | DMDEC | QDPSSC IDGQCVNTEGSYNCF CTHPMVLDASEKR | CI | 1140-1180 |
| 15 | QAEEC | GILNGC ENGRCVRVQEGYTCD CLDGYHLDTAKMT | CF | 1294-1334 |
| 16 | DVNECDELNNRMSLC | KNAKCINTDGSYKCL CLPGYVPSDKPNY | CT | 1335-1379 |

```
        ID                                 Y          Y
      D  EC         C    G C N   GS  C   C G        C          consensus
      VN                     F          F
```

DINECKDPSNINGGC  SQICDNTPGSYHCS  CKNGFVMLSNKKD  CK   human protein S
DVDEC  AEPGLSHCHALATCVNVVGSYLCV  CPAGYRGDGWH  CE   human uromodulin
NSD SEC  PLSHDGYCLHDGVCMY IL DKYACN  CVVGYIGER            human EGF
                                  EK
                                          CQYRDLKWWELR

FIG. 5b.

| repeat no. | | amino acid no. |
|---|---|---|
| a | EEKGPCYRLVSSGRQCMYPLSVHL TKQLCCCSVGKA GPHCEK CPLPGTAAFKEICPGGM GYTVS G | 348- 412 |
| b | EEKKECYNLNDASLCDNVLAPNV TKQECCCTSGAGWGDNCEIFPCPVLGTAEFTEMCPKGK GFVPA G | 1017-1084 |
| c | EETDVYQDLCWEHLSDEYVCSRPLVGKQTTYTECCCLYGEAWGMQCAL CPLKDSDDYAQLCNIPVTGRRQPYG G | 1190-1262 |
| | C C L T CCC G G C CP C G G | consensus |

FIG. 7.

|   | a | b | c | d |   |
|---|---|---|---|---|---|
| $M_r \times 10^{-3}$ | | ● | | | |
| | | | | | ]230-260 |
| 200- | | | | | |
| | | | | | ]150-160 |
| 92- | | | | | ]90-100 |
| 69- | | | | | |
| | | | | | -50 |
| 46- | | | | | |

ISOLATED NUCLEOTIDE SEQUENCE EXPRESSING HUMAN TRANSFORMING GROWTH FACTOR-β1-BINDING PROTEIN

FIELD OF THE INVENTION

This invention relates to the field of protein biochemistry. More particularly, it relates to a component of the large, latent complex of the material known as Transforming Growth Factor β1 ("TGF-β1" hereafter), denoted TGF-β1 binding protein ("TGF-β1-BP" hereafter), and nucleotides, such as genomic DNA, cDNA and mRNA which code for, express, or translate the TGF-β1-BP. The protein is useful, e.g., in generating antiserum for binding to the aforementioned complex, or a labeled probe in assays therefore, as well as in other uses described herein.

BACKGROUND AND PRIOR ART

Transforming growth factor-β(TGF-β) is a family of structurally related molecules denoted TGF-β1, -β2, -β3, -β4 and β5; these molecules are in turn more distantly related to several other factors including inhibins-/activins, Müllerian inhibitory substance, bone morphogenic proteins, the product of the decapentaplegic complex of Drosophila and Vgl of Xenopus. See Roberts, et al. Handbook of Experimental Pharmacology, Volume 95, (in press, 1990). TGF-β was originally identified because of its ability to stimulate anchorage independent growth of NRK cells in synergy with TGF-α, Roberts, et al., Fed. Proc. 42: 2621-2626(1983). It has subsequently been found to stimulate or to inhibit growth and differentiation of many different cell types. See Roberts, et al., 1990, supra.

TGF-βs bind to at least three different receptor-like molecules; two smaller species of 53 and 73 kDa, denoted type I and type II receptors, respectively, and one larger proteoglycan-like structure denoted type III receptor or beta-glycan (Cheifetz, et al., Cell 40: 409-415 (1987); Cheifetz, et al., J. Biol. Chem. 264: 2272-2278 (1988); Andres, et al., J. Cell. Biol. 109: 3137-3146 (1989); Segarini, et al., J. Biol. Chem. 263: 8366-8370 (1988)). The biological effects of TGF-β seems to be mediated by the type I receptor (Boyd and Massague, J. Biol. Chem. 264: 2272-2278 (1989)).

TGF-βs are 25 kDa disulfide-bonded dimeric molecules which are synthesized and secreted as inactive high $M_r$ complexes (Pircher, et al., Cancer Res. 44: 5538-5543 (1984); Pircher, et al., Biochem. Biophys. Res. Commun. 136: 30-37 (1984); Wakefield, et al., J. Cell Biol. 105: 965-975 (1987)). The large latent complex of TGF-β1 from human platelets has been purified and characterized as described by Miyazono, et al., J. Biol. Chem. 263: 6407-6415 (1988), the disclosure of which is incorporated by reference. In this complex the TGF-β1 molecule is noncovalently associated with a disulphide-bonded complex of a dimer of the N-terminal propeptide of the TGF-β1 precursor and a third component denoted the TGF-β1 binding protein (TGF-β1-BP). The platelet-derived TGF-β1-BP was found to occur as several species of sizes between 125 and 160 kDa. See Miyazono, et al., supra.

The fact that TGF-βs have dramatic effects on growth and differentiation of most cell types, together with the observation that they are synthesized by many different cell types, indicate that the activation of TGF-βs from their high $M_r$ latent complexes must be an important regulatory step in vivo. In vitro, activation is achieved e.g. by acidification to pH values below 4, as described by Pircher, et al., and Miyazono, et al., supra. In vivo such low pH values are rarely found extracellularly. The in vivo mechanism of activation is not fully understood; possible mechanisms include proteolysis or perturbation of the carbohydrate structures of the TGF-β1 propeptide in the latent complex. See Miyazono and Heldin, Nature 338: 158-160 (1989), the disclosure of which is incorporated by reference, and Lyons, et al., J. Cell Biol. 106: 1659-1665 (1988).

SUMMARY OF THE INVENTION

The invention describes the isolation and characterization of the aforementioned TGF-β1-BP; particularly the fibroblast and platelet forms of the molecule. Using complexes of proteins obtained from platelets, the platelet form of the molecule was isolated, fragmented, and its primary structure (i.e., amino acid sequence) deduced. The fragments were used to develop DNA probes, which were then used to obtain a nucleotide sequence, from a total cDNA library of fibroblasts, to secure a substantially pure nucleotide sequence expressing the fibroblast form of the molecule. An amino acid sequence was deduced from the cDNA clone, and it was found that the sequence for the platelet form of the molecule was contained entirely within the 60% of the fibroblast form, referring to the C terminal end of the fibroblast form. The fibroblast form of the molecule is characterized by a molecular weight of from about 170 to about 190 kilodaltons, as compared to the platelet form, which has a molecular weight of from about 125 to about 160 kilodaltons. The cDNA clones isolated from the library are used to transfect recipient host cells, and the binding protein is then expressed. The nucleotide sequence is incorporated into vectors, e.g., to accomplish the transfection.

Unique features of the protein include a series of sixteen repeats of a domain referred to herein as an "epidermal growth factor like" domain, as well as three repeats of a domain not previously noted in the art.

BRIEF DESCRIPTION OF THE FIGURES

FIG. 3 shows Northern Blot analysis of TGF-β1-BP mRNA.

FIG. 4b gives nucleotide sequence and amino acid sequences for cDNA expressing fibroblast TGF-β1-BP and the BP itself.

FIGS. 5(a)-(c) show various aspects of the protein. In FIG. 5(a), the EGF-like repeat sequences are aligned. In FIG. 5(b), a previously unrecognized repeat sequence, which occurs three times in the protein, is aligned. FIG. 5(c) shows the position of the repeats given in FIGS. 5(a) and 5(b) in the complete protein, as well as other fragments, and possible N-glycosylation sites.

FIG. 6(a) depicts immunoprecipitation studies of COS cells transfected with the cDNA. FIG. 6(b) shows endo H treatment of the precursor form of TGF-β1-BP from the transformed cells. FIG. 6(c) shows the immunoprecipitation of the protein from fibroblasts and immunoblotting of the protein from platelets.

FIG. 7 depicts interaction of labeled, purified TGF-β1, and the so-called "large latent TGF-β1 complex".

DETAILED DESCRIPTION OF PREFERRED EMBODIMENTS

Example 1

Figure 1:
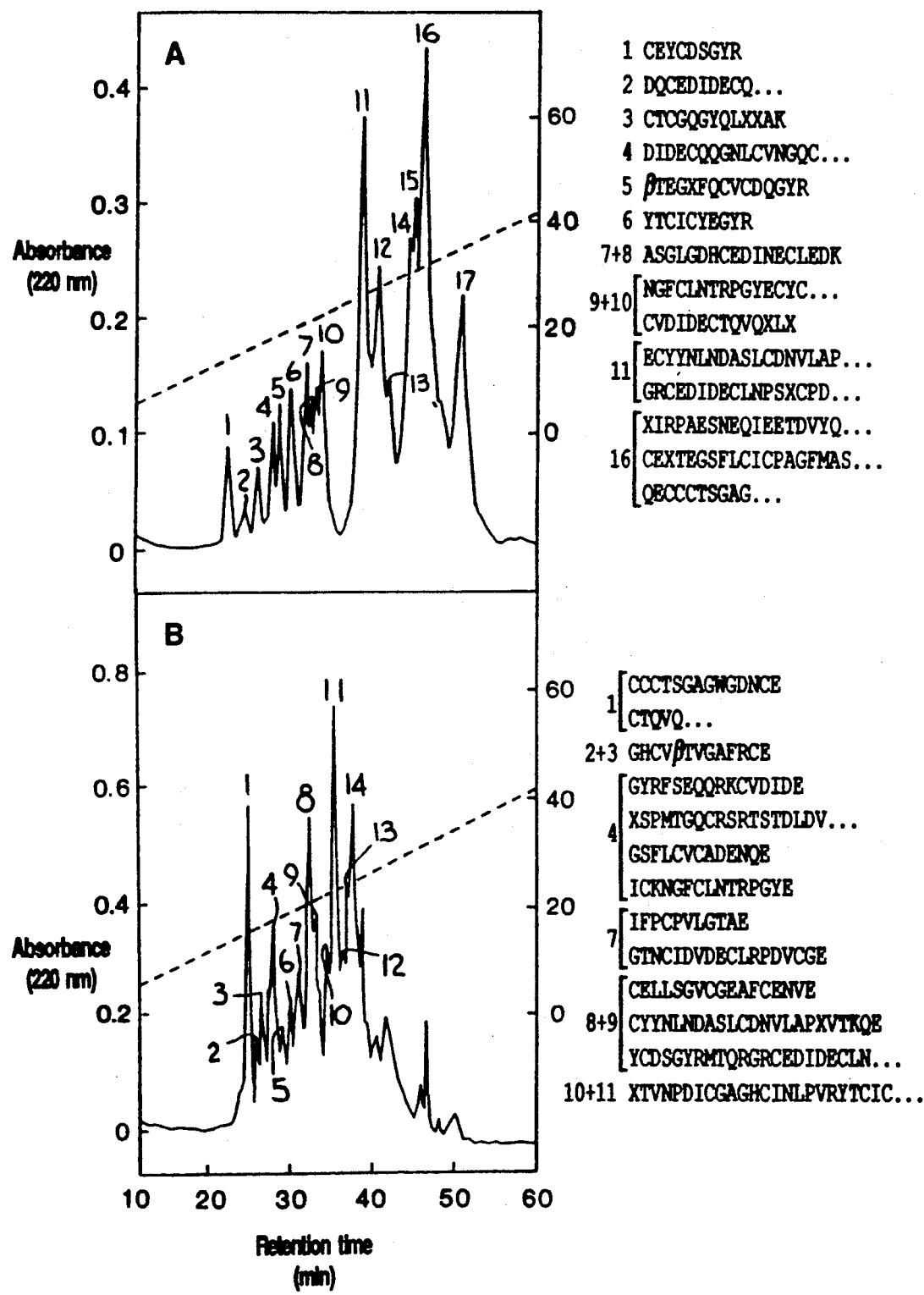
FIG. 1 shows HPLC (high performance liquid chromatography) analysis, including separation and sequencing of proteolytic fragments of the platelet TGF-β1-BP described herein.

TGF-β1-BP was purified from human platelets as described by Miyazono, et al., JBC 263(13): 6407–6415 (1988), the disclosure of which is incorporated by reference herein. For ease of review, the protocol is repeated here. It is pointed out that, following Miyazono, the TGF-β1-BP is purified as part of a complex of various molecules. Isolation of the individual protein described herein is discussed in Example 2, which follows.

Approximately 800–1000 liters of human blood were used to derive 15 liters of platelet protein, as a nonadsorbed fraction from CM-Sephadex chromatography, following Heldin, et al., Meth. Enzymol 147: 3–13 (1987). This material was then processed via QAE-Sephadex following Miyazono, et al, J. Biol. Chem. 262: 4098–4103 (1987). A complex of latent TGF-β1 ("L-TGFβ1") was eluted therefrom, between 250 and 800 mM of NaCl in 10 mM phosphate buffer, at pH 7.4. Ammonium sulphate (209 g/liter; 35% of saturation) was added to the QAE-Sephadex column eluate. After equilibration for 2 hours at 4° C., the sample was centrifuged at 2075×g for 15 minutes. The precipitates were collected and resuspended in about 100 ml of 150 mM NaCl, 10 mM Tris-HCl, pH 7.4, and dialyzed extensively against the same buffer. An equal volume of 2M ammonium sulfate, 10 mM Tris-HCl, pH 7.4, was added to the sample which was then centrifuged at 2075×g for 15 minutes. The supernatant was applied to a 20 ml column of octyl-Sepharose (Pharmacia LKB Biotechnology Inc.), pre-equilibrated with 1M ammonium sulfate, 10 mM Tris-HCl, pH 7.4. The column was washed with the same buffer and eluted with 10 mM Tris-HCl, pH 7.4. The eluate from octyl-Sepharose chromatography was dialyzed against 10 mM phosphate buffer, pH 6.8, 0.01 mM CaCl$_2$, and loaded onto a high performance hydroxylapatite column (100×7.8 mm, Bio-Rad) equipped with a guard column (50×4.0 mm, Bio-Rad). The column was equilibrated with 10 mM phosphate, pH 6.8, 0.01 mM CaCl$_2$ and eluted with a gradient of 10–300 mM phosphate, pH 6.8, 0.01 mM CaCl$_2$ at a flow rate of 0.5 ml/min. The fractions containing high concentration of L-TGF-β1 were pooled, concentrated to 100 μl using Centricon 10 microconcentrator (Amicon Copr.), and applied to a Superose 6 column (HR 10/30, Pharmacia LKB Biotechnology Inc.). The column was equilibrated with 500 mM NaCl, 10 mM Tris-HCl, pH 7.4, and eluted at a flow rate of 0.5 ml/min. The fractions containing L-TGF-β1 were pooled and mixed with an equal volume of 2.8M ammonium sulfate (HPLC grade, Bio-Rad), 100 mM phosphate, pH 6.8, and applied to an alkyl-Superose HR 5/5 column (Pharmacia LKB Biotechnology Inc.) equilibrated in 1.4M ammonium sulfate in phosphate buffer. The column was eluted at a flow rate of 0.5 ml/min with a gradient of 1.4–0M ammonium sulfate in 100 mM phosphate, pH 6.8.

This protocol yielded a complex containing the TGF-β1 binding protein as well as TGF-β1. Activity was measured using a [$^3$H]-thymidine incorporation assay as described by Miyazono, et al., J. Biol. Chem. 263(13): 6407–6415 (1988), the disclosure of which is incorporated by reference herein.

Example 2

The protein complex obtained in Example 1 was then used to isolate pure TGF-β1-BP therefrom. It was found that free TGF-β1-BP elutes immediately after the large, L-TGF-β1 complex elutes from the alkyl superose column. This free TGF-β1-BP was then treated further, to purify it and to determine its amino acid sequence.

Approximately 75 μg portions of pure TGF-β1-BP were desalted on a C4 narrow-bore reversed-phase column (Brownlee, Aquapore BU-300, 2.1×30 mm), eluted in 0.1% trifluoroacetic acid (TFA) with a gradient of acetonitrile; the material was then dried in a Speedvac Concentrator and redissolved in 200 μl of 6M guanidine-HCl, 0.25M Tris-HCl pH 8.5, 1 mM EDTA containing 100 μg dithiothreitol. The solution was flushed with N$_2$ for 20 seconds and left at room temperature for 3 hours, at which time 2 μl of 4-vinyl pyridine was added. After a further incubation for 3 hours at room temperature, the sample was desalted by chromatography on the C4 column as described above. The volatile solvent was evaporated and TGF-β1-BP was then digested at 37° C. for 14 hours with TPCK-trypsin (Sigma, St. Louis, Mo.) at a substrate to enzyme ratio of 50:1 (w/w) in 200 μl of 0.1M ammonium bicarbonate containing 2M urea. The tryptic fragments were immediately loaded on a C4 narrow-bore, reversed-phase HPLC column eluted with a linear gradient of acetonitrile in 0.1% TFA. Non-homogeneous peptides were re-run on the HPLC narrow-bore reversed-phase column under different conditions. The column temperature was kept at 35° C., the flow rate was 100 μl min and the effluent monitored at 220 nm. Fractions were collected manually in polypropylene tubes. Peptides were also isolated from TGF-β1-BP fragmented with staphylococcal V8 protease (Boehringer Mannheim Biochemica, FRG) by similar methods. The amino acid sequence of the peptides were determined by use of automated gas-phase sequencer (Applied Biosystems Protein Sequencer, model 470A, with an online PTH-analyzer, model 120A).

The analysis of the peptide fragments, with deduced amino acid sequences are shown in FIG. 1.

Figure 2:
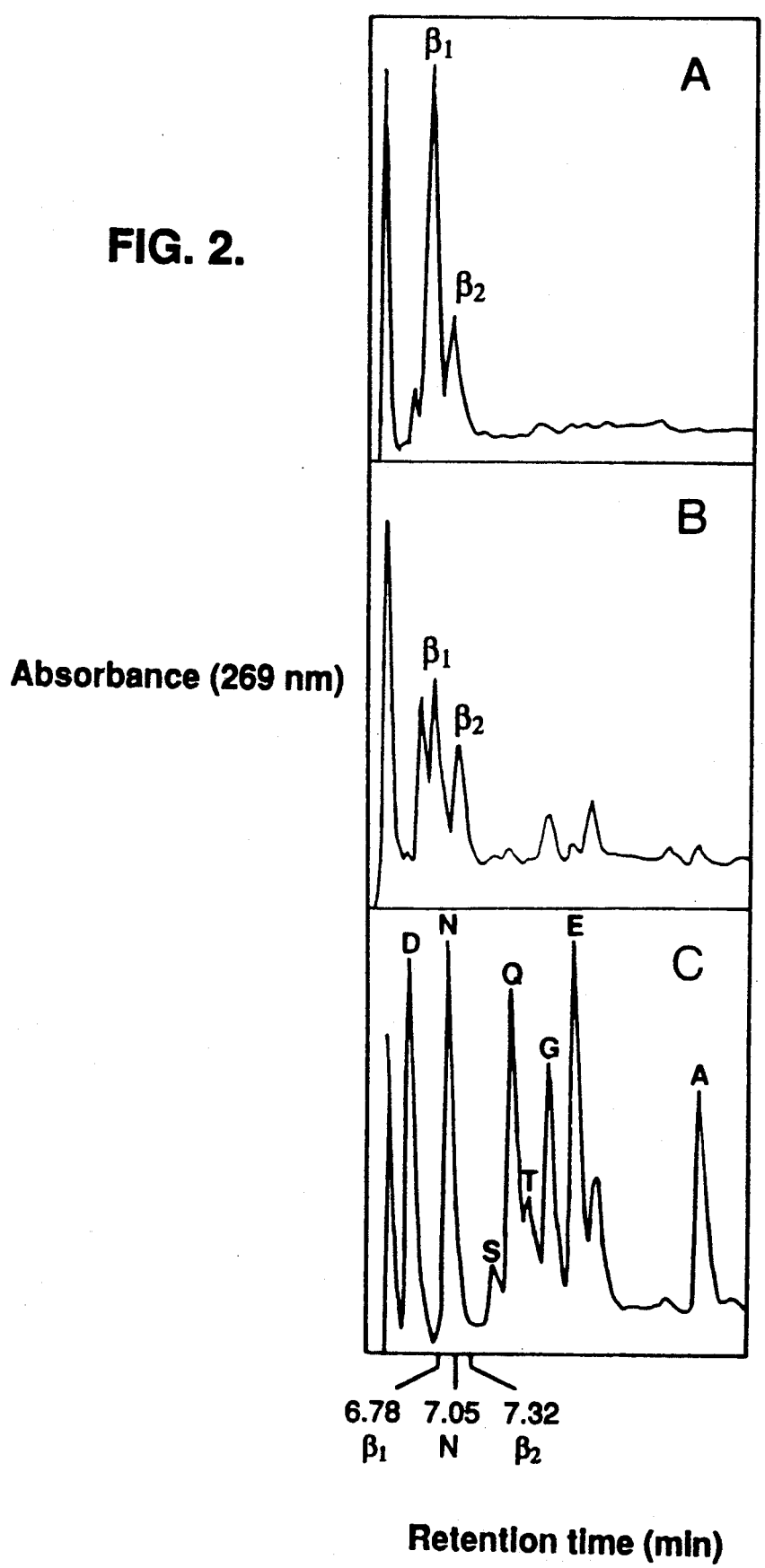
FIG. 2 presents data proving the presence of a β-hydroxylated asparagine residue in TGF-β1-BP.

In the sequencing protocol, the trypsin and staphylococcal V8 protease were used because attempts to determine the N-terminal amino acid sequence indicated that the N-terminus was blocked. As shown in FIG. 2, 27 peptides were sequenced. Quite surprisingly, 22 of these showed similarity to the EGF domain. In addition, several contained the known consensus sequence for beta-hydroxylation of asparagine/aspartic acid residues found in many vitamin K dependent proteins involved in blood coagulation (see Drakenberg, et al., Proc. Natl. Acad. Sci. USA 80: 1802–1806 (1983)). As a result of this observation, the fragments were analyzed further to determine if they contained this unusual post-translational amino acid. The reversed phase chromatogram of cycle 1 of sequence determination of peptide fragment number 5 showed no peaks corresponding to phenylthiohydantoin (PTH) derivatives of common amino acids, which will be seen in FIGS. 2(b) and 2(c). An extra double peak was found early in the chromatogram, and this coeluted exactly with the PTH derivative of hydroxylated asparagine, which had been run as a standard. This will be seen by comparing FIGS. 2a and 2b. A similar pattern, observed in cycle 5 of V8 peptides 2 and 3, leads to the conclusion that the TGF-β1-BP contains hydroxylated asparagine residues.

Example 3

Following isolation and purification of the TGF-β1-BP, cDNA expressing or coding for this molecule was obtained.

For screening of a cDNA library, a 24 amino acid peptide sequence (FIG. 1; tryptic fragment No. 11 and V8 fragment No. 8 and 9, starting with the sequence ECYY and ending with TKQE), was chosen for preparation of a probe by using PCR in accordance with Lee, et al., Science 239: 1288-1291 (1988). Briefly, PCR was performed using first strand cDNA prepared from human fibroblasts AG1518 (Human Genetic Mutant Cell Repository, Camden, N.J.), and Taq polymerase (Perkin Elmer Cetus, Norwalk, Conn.). After 30 cycles of PCR, DNA was separated on a 2.5% agarose gel; the material of approximately 50-110 bp was used for a second round of PCR amplification. A fragment of the expected size of 86 bp (72 bp and added restriction sites) was then visualized after separation on a 2.5% agarose gel and recovered by electroelution. Recovered DNA was ligated with M13 vectors for sequence analysis, and the obtained sequence was shown to code for the 24 amino acid peptide used as a template.

A human foreskin fibroblast λgt10 cDNA library (Claesson-Welsh et al. Proc. Natl. Acad. Sci. 86: 4917-4921 1989) was screened with the PCR probe labeled by the Multiprime DNA labeling system (Amersham, UK). Hybridization to nitrocellulose replica filter papers were performed in 40% formamide, 5×SSC (1×SSC contains 15 mM sodium citrate and 150 mM NaCL pH 7.4), 5×Denhardt solution, 0.1% SDS and 50 μg/ml of salmon sperm DNA at 37° C. overnight, using about 500,000 cpm of the $^{32}$P-labeled probe/ml of hybridization solution. The filters were washed in 2×SSC, 0.1% SDS at 37° C. three times for 20 minutes, dried and exposed to Fuji X-ray films. About $10^7$ bacteriophage plaques were screened, yielding 6 positive clones. The largest clone identified was 5.1 kilobase pairs long, was denoted BPA 13, and was purified following Maniatis, et al., Molecular Cloning: A Laboratory Manual (Cold Spring Harbor) and was sequenced following Sanger, et al. Proc. Natl. Acad. Sci. 74: 5463-5467 (1977) on both strands using Sequenase (United States Biochemical Corporation, Cleveland, Ohio), after subcloning into pUC19 as described by Yannisch-Perron, et al., Gene 33: 103-119 (1985). The sequence is presented in FIG. 4b, together with a deduced amino acid sequence.

Example 4

Total messenger RNA ("mRNA") was cultured from human fibroblasts (AG1518) by using the guanidium thiocyanate method of Chirgwin, et al., Biochemistry 18: 5294-5299 (1979). mRNA was selected by using oligo-dT cellulose (Pharmacia LKB Biotechnology Inc., Uppsala, Sweden) as described by Maniatis et al, supra.

For Northern blotting mRNA (2.5 μg) was denatured at 55° C. for 15 minutes with formaldehyde and formamide, electrophoresed on a 1% agarose gel in the presence of formaldehyde and transferred to nitrocellulose filter. Hybridization was performed in 50% formamide, 5×SSC 5×Denhardt solution, 0.1% SDS, 50 mM sodium phosphate buffer pH 6.5, and 0.1 mg/ml salmon sperm DNA at 37° C. overnight by using a $^{32}$P-labeled pVU II fragment (bp no. 2900-3834 of BPA13) as a probe. The filter paper was washed 3 times for 30 minutes in 0.1×SSC, 0.1% SDS at 55° C., dried and exposed to Amersham Hyperfilm MP.

Figure 3:
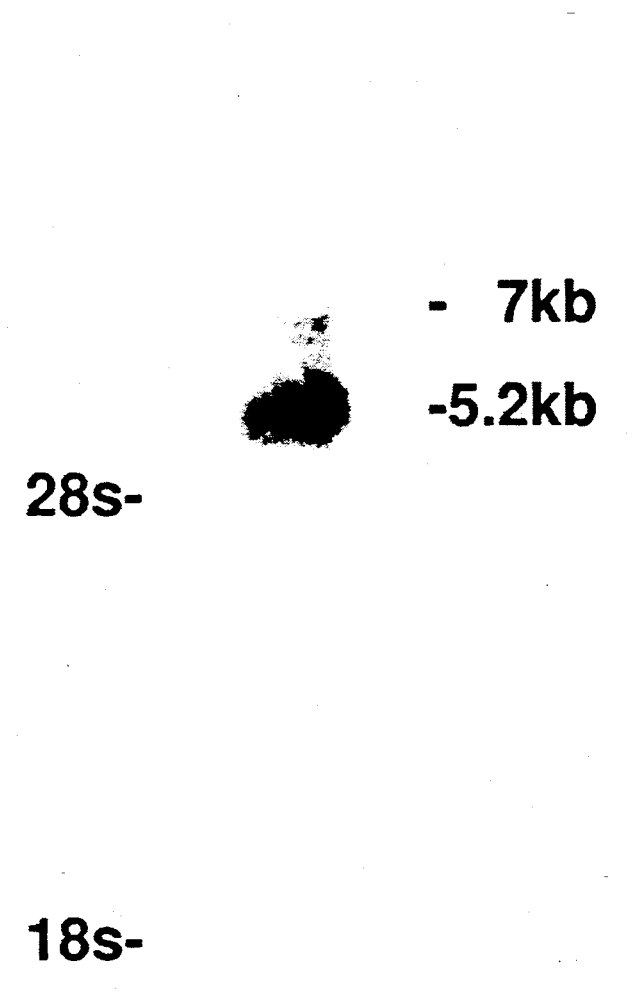

As shown in FIG. 3, when BPA 13 was used as a probe, two bands of 7 and 5.2 kilobases in length were obtained. From this data, it is concluded that BPA 13 is similar in length to the shorter of the two mRNA species.

Example 5

The nucleotide sequence of BPA 13 was deduced following the methods set forth at the end of Example 3, supra.

These methods showed that BPA 13 is 5089 bp in length consisting of an open reading frame of 4182 bp, flanked by untranslated sequence of 90 bp in the 5'end, 803 pb in the 3'end and 14 bp of EcoRI adaptor sequences (FIG. 4). the 3' untranslated sequence contained a polyadenylation signal, AATAAA, but the poly A tail was missing. Two ATTTA sequences, implied in instability and rapid turnover of the corresponding mRNA molecules (Shaw and Kamen, Cell 46: 659-667) were found. In the 5' part of the open reading frame, 2 possible initiating methionine codons were present. The first ATG followed the rules for translational initiation described by Kozak, Cell 44: 283-292 (1986), but the second did not (FIG. 4b). It appears that translation is initiated at the first ATG. The deduced amino acid sequence predicts that TGF-β1-BP contains 1394 amino acids starting with a hydrophobic leader sequence. The signal sequence is probably cleaved between amino acids 20 and 21 which would be a preferred site according to the predictions of von Heine in J. Mol. Biol. 173: 243-251 (1984). The calculated $M_r$ of the primary translational product of TGF-β1-BP without signal sequence is about 151,000.

Figure 4A:
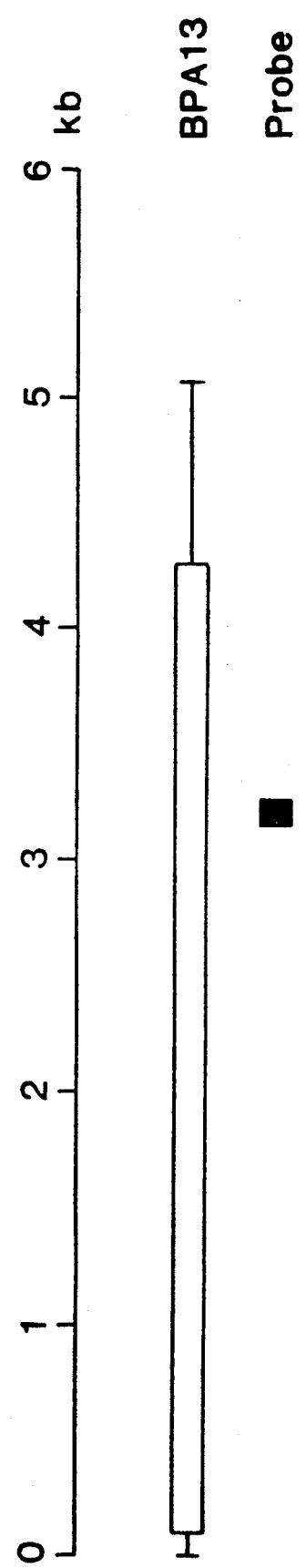
FIG. 4a depicts cDNA clone BPA 13 schematically, with translated and untranslated regions shown with "☐" and "—", respectively.
Figure 4B-4:
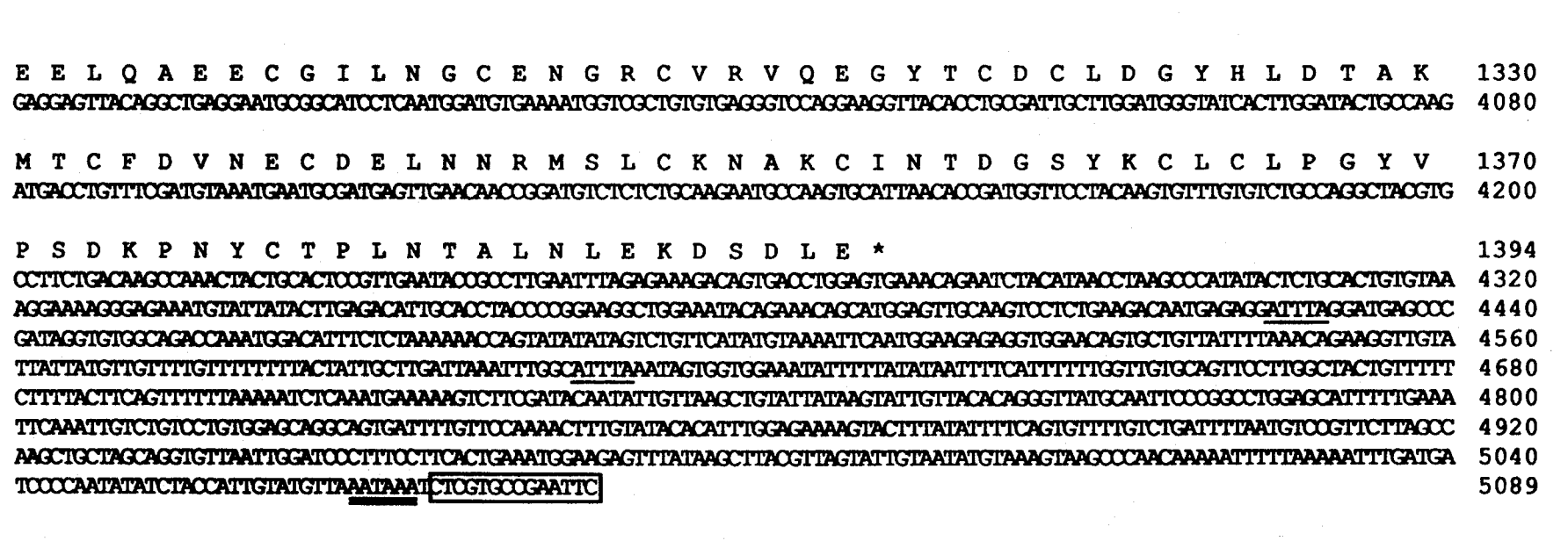

FIGS. 4(a) and 4(b) give more information regarding this cDNA sequence and the deduced amino acid sequence of TGF-β1-BP. Specifically, the structure of the cDNA clone BPA 13 is schematically outlined in (a) with its translated (□) and untranslated (−) regions. The localization of the probe used for screening of the cDNA library is also indicated (■).

The nucleotide sequence and the deduced amino acid sequence of BPA13 is shown in FIG. 4b. Nucleotides and deduced amino acids are numbered to the right; the amino acids are numbered starting with the proposed initiating methionine residue and the putative N-terminal of the mature protein is indicated by an arrow head (▼). Possible N-glycosylation sites are overlined with solid lines and an RGD sequence with a broken line. Two stop codons in the 5' untranslated sequence and the stop codon that ends the open reading frame are marked with (*). In the 3' untranslated area, two ATTTA motifs are underlined and a poly A additional signal (AATAAA) is indicated with two lines. The EcoRI adaptor sequence is boxed.

Example 6

Further studies were carried out on the isolated TGF-β1-BP molecule, once the amino acid sequence of its fragments and the predicted amino acid sequence were found.

The most remarkable feature of the TGF-β1-BP sequence is that 64% of it is made up of repeat sequence rich in cysteine residues; there are 16 EGF-like repeats (FIG. 5a) and in addition, 3 repeats of an about 70 amino acid long motif containing 8 cysteine residues have not been found in any other sequence in the data base (Genebank release no. 60, Protein Identification Resource release no. 21) (FIG. 5b). The two types of repeat sequences seem to be distantly related to each other, in particular, the region in the middle of the novel repeat which is rich in cysteine and glycine residues, is also found in EGF. The 16 EGF-like repeats were more similar to each other than to other known EGF-like repeat sequences (see Appella et al., 1988, for a review of EGF-like repeats), and fifteen of them were found to contain the consensus sequence for β-hydroxylation of asparagine residues (Stenflo et al. Proc. Natl. Acad. USA 84: 368-372 (1978) (FIG. 5a). Amino acid sequencing of platelet TGF-β1-BP led to the identification of β-hydroxylated asparagine residues in repeats 4 and 8 (FIG. 5A). The EGF-like repeat No. 9 was found to contain an RGD sequence; this sequence in matrix proteins has been found to mediate interactions with cell surface receptors, integrins (Ruoslahti, et al., Science 288: 491–497 (1978). One of the novel cysteine-rich motifs (FIG. 5B, repeat a) was found to contain a sequence of 8 amino acids which is identical to a sequence in the B2 chain of laminin (Sasaki, et al., J. Biol. Chem. 262: 17111–17117 (1987)). The 36% non-repetitious sequence of TGF-β1-BP did not show any similarity to other known sequences.

Figure 5C:
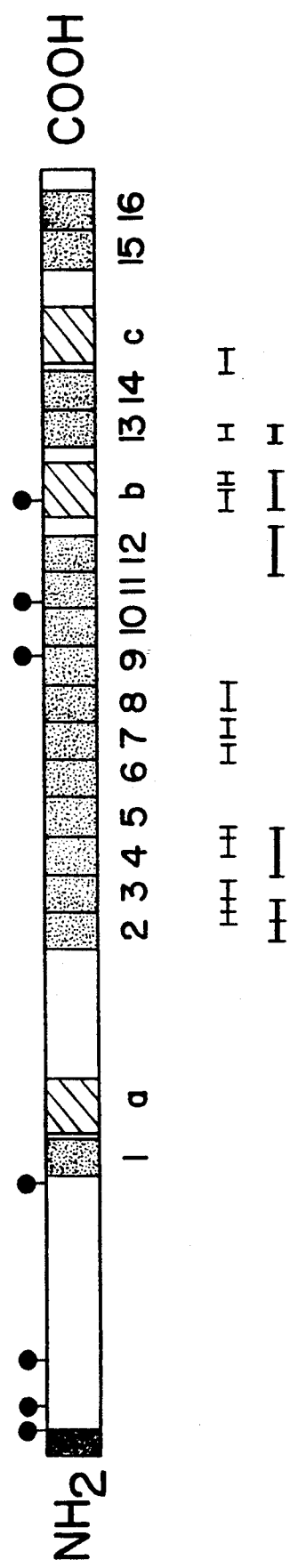

A total of 322 amino acids were identified by sequencing of peptides from human platelet TGF-β1-BP; the obtained cDNA sequence matched the protein sequence in each of these proteins. Of the 7 potential N-glycosylation sites in the protein sequence deduced from the cDNA, the most carboxy-terminal one was covered by the sequenced peptides (FIG. 5c). Since no amino acid could be assigned to this position upon sequencing of the corresponding tryptic and V8 peptides (FIG. 1; peptides nos. 11 and 8 and 9, respectively), this asparagine residue is probably glycosylated in the mature protein. As illustrated in FIG. 5C, the sequences of all peptides derived from platelet TGF-β1-BP are localized in the carboxy-terminal 60% of the fibroblast sequence. This is consistent with the difference in size between the platelet (125-160 kDa) and fibroblasts 170-190 kDa proteins, as discussed infra.

The alignment of the EGF-like repeat sequences of TGF-β1-BP from human fibroblasts is shown, in some detail in FIG. 5. The repeat sequences are numbered consecutively from the N-terminal (left); the numbers of the amino acids in the TGF-β1-BP sequences are also indicated (right). Amino acid residues which are present in ≧12 of the 16 repeat sequences are shown as a consensus sequence. Asparagine residues found to be β-hydroxylated in the platelet form of TGF-β1-BP are underlined as well as an RGD sequence. For comparison, EGF-like sequence of human protein S (amino acids 116–159 in the protein), human uromodulin (amino acids 84–125 in the protein) and human EGF.

An alignment of a second, previously unrecognized type of repeat sequence in TGF-β1-BP is shown in FIG. 5(b). The repeats are indicated by letters (left) and the numbers of the amino acids in the TGF-β1-BP sequences are shown (right). The amino acid residues which are identical in the three repeats are shown as a consensus sequence. An eight amino acid sequence in repeat a, that is identical to a sequence in laminin B2 is underlined.

A schematic representation of TGF-β1-BP from human fibroblasts is shown in FIG. 5(c) signal sequence (■), 16 EGF-like repeats (▦), 3 repeats sequences of another type (▨) and 7 possible N-glycosylation sites (♥) are indicated. The repeat sequences are identified with numbers and letters (see FIG. 5A and B). The localization of the amino acid sequences of tryptic (⊢⊣) and V8 protease (⊢⊣) fragments of TGF-β1-BP purified from human platelets are indicated.

Example 7

Experiments were carried out to study the transient expression of TGF-β1-BP in eukaryotic cells. To do this a TGF-β1-BP cDNA (bp 3-4943), containing the translated part, was cloned into SV40 based expression vector pSV7d described by Truett, et al., DNA 4: 333-349 (1985). For transient expression, this construct was transfected into COS cells by the calcium phosphate precipitation method following Wigler, et al., Cell 16: 777-785 (1979). Transfected COS cells were analyzed for expression of TGF-β1-BP 2 days after transfection.

The COS-1 cells (American Type Culture Collection) and human fibroblasts (AG1518), and COS-1 cells transfected by TGF-β1-BP cDNA were cultured in Dulbecco's modified Eagle's medium (DMEM) containing 10% fetal bovine (FBS, Flow Laboratories, Irvine, Scotland), 100 units of penicillin and 50 μg of streptomycin per ml at 37° C. in a 5% $CO_2$ incubator.

To facilitate the measurement of transient expression of the protein, cells in 75 or 175 $cm^2$ tissue culture flasks were labeled with 0.2 mCi $^{35}S$-methionine and $^{35}S$-cysteine (Amersham, UK) per ml in methionine and cysteine-free DMEM (3 or 6 ml) containing 10% FBS at 37° C. for 4 hours. After 4 hours of labeling, medium was collected and cells were washed three times by ice-cold phosphate buffered saline (PBS). Cells were detached and lysed by adding 1 or 2 ml of 0.5% Triton X-100, 0.5% deoxycholate, 20 mM Tris-HCl, pH 7.5, 150 mM NaCl, 10 mM EDTA, 1% Trasylol (Bayer, Leverkusen, FRG), and 1 mM phenylmethylsulfonyl fluoride (Sigma, St. Louis, Mo.). Lysed cells were incubated at 4° C. for 15 minutes and centrifuged at 10,000×g at 4° C. for 30 minutes. The medium and supernatants form lysed cells were precleared with non-immune rabbit serum and heat-killed, formalin-fixed *Staphylococcus aureus* Cowan 1 bacteria. Ten μl of rabbit antiserum against purified TGF-β1-BP from human platelets (Ab39) or 10 μl of Ab39 plus 1 ug of TGF-β1-BP was added to 1 ml of precleared samples and incubated under gentle shaking at 4° C. for 14 hours. Protein A-Sepharose (Pharmacia, Biotechnology, Uppsala, Sweden) was used to precipitate immune complexes. The protein A-Sepharose beads were washed three times with 1% Triton X-100, 1% deoxycholate, 0.1% SDS, 50 mM Tris-HCl, pH 7.5, 150 mM NaCl and 10 mM EDTA, once with 1% Triton X-100, 0.5M NaCl and 20 mM Tris-HCl, pH 7.5, and once with distilled water. The immune complexes were eluted from the beads by boiling for 5 minutes in SDS-sample buffer containing 4% SDS, 0.2M Tris-HCl, pH 8.8, 0.5M sucrose, 0.01% bromophenol blue and 2% β-mercaptoethanol and analysed by SDS-polyacrylamide gel electrophoresis using 5–10% gradient slab gels (Blobel and Dobberstein, 1975). Gels of immunoprecipitates were treated for fluorography by being soaked in Amplify (Amersham, UK), dried and exposed to Amersham Hyperfilm MP. Gels of purified TGF-β1-BP from human platelets were electrophoretically transferred to nitrocellulose papers and subjected to immunoblotting following Terracio, et al., J. Cell Biol 107: 1947-1957 (1988) using an antibody against a synthetic peptide of platelet TGF-β1-BP (Ab37); amino acids 1111–1122 of TGF-β1-BP); bound antibodies were visualized using $^{125}$I-Protein A followed by autoradiography.

Samples immunoprecipitated with Ab39 from $^{35}$S-methionine- and $^{35}$S-cysteine-labeled COS cells transfected with TGF-β1-BP cDNA, were incubated with 1 mU Endo H (Miles Laboratories Inc. Naperville, Ill., USA) in a buffer containing 0.1M Tris-HCl, pH 6.8, 0.1% SDS, and 2% β-mercaptoethanol at 37° C. for 6 hours. Samples were analyzed by SDS-polyacrylamide gel electrophoresis and fluorography.

TGF-β1 (R & D Systems Inc., Minneapolis, Minn.) was labeled with $^{125}$I (Amersham, UK) by the chloramine-T method to a specific activity of 80 μCi/μg. TGF-β1-BP and the large latent TGF-β1 complex was purified from human platelets (following Miyazono, et al., supra) and desalted by chromatography on Superose 6 in 500 mM NaCl, 10 mM 2-hydroxyethyl-piperazine ethane sulfonate (Hepes) pH 7.5. One μg of TGF-β1-BP or 250 ng of the large latent TGF-β1 complex were incubated with 5 ng of $^{125}$I-TGF-β1 in 100–200 μl of 128 mM NaCl, 5 mM KCl, 1.2 mM CaCl$_2$, 1.2 mM MgSO$_4$ and 50 mM Hepes, pH 7.4, at 4° C. for 2 hours. Cross-linking was performed by incubation with 0.25 mM final concentration of DSS (Pierce, Rockford, Ill., USA) for 15 minutes at 20° C.; the reaction was quenched by adding 20 mM final concentration of Tris-HCl buffer, pH 7.4. Samples were immunoprecipitated by Ab39 and protein A-Sepharose, eluted by boiling for 5 minutes in SDS-sample buffer, and analyzed by SDS-polyacrylamide gel electrophoresis under reducing conditions followed by autoradiography.

The ability of TGF-β1-BP to inhibit the binding of $^{125}$I-TGF-β1 to cells was analyzed using NRK cells (NRK 49F, American Type Culture Collection) seeded in 24 well plates (Costar, Badhoevedorp, Netherlands) precoated with gelatin. Confluent cell cultures were maintained serum-free for one day and then washed twice with ice-cold binding buffer containing 25 mM Hepes, pH 7.4, 0.1% bovine serum albumin (BSA, fraction V, Boehringer Mannheim Biochemica, FRG) in PBS containing 0.1 mg/ml CaCl$_2$ and 0.13 mg/ml MgCl$_2$. Cells were then incubated with 25 pM $^{125}$I-TGF-β1 together with various amounts of unlabeled TGF-β1, or desalted TGF-β1-BP, in 0.2 ml of binding buffer of 3 hours at 4° C. After washing three times with the ice-cold binding buffer, cell-bound radioactivity was solubilized for 20 minutes at 4° C. with 0.5 ml 1% Triton X-100, 10% glycerol, 0.01% BSA, 20 mM Hepes, pH 7.4 and determined in a γ-counter.

Figure 6A:
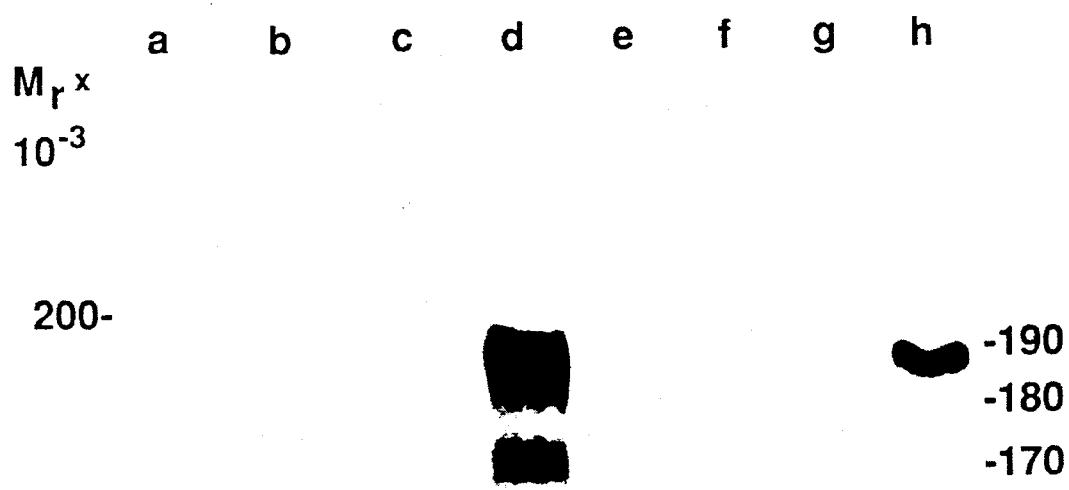
FIGS. 6(a)-(c) concern studies on cells transformed with cDNA for the protein.

The immunoprecipitation studies described supra, using the transfected COS cells, revealed an SDS-gel electrophoresis band of about 170–190 kilodaltons in cell lysate, and 190 kDa in the conditioned media. These components were similar in size to TGF-β1-BP purified from the fibroblasts described supra, and depicted in FIGS. 6(a) and 6(c). In contrast, platelet TGF-β1-BP, analyzed following immunoblotting in parallel, revealed a species of 125–160 kDa, as shown in FIG. 6(c). The untransfected COS cell contained no components immunoreactive with the antisera.

Figure 6B:
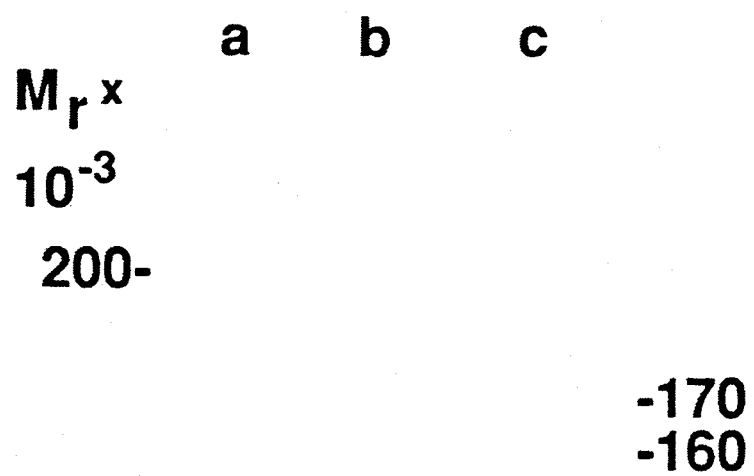
Figure 6C:
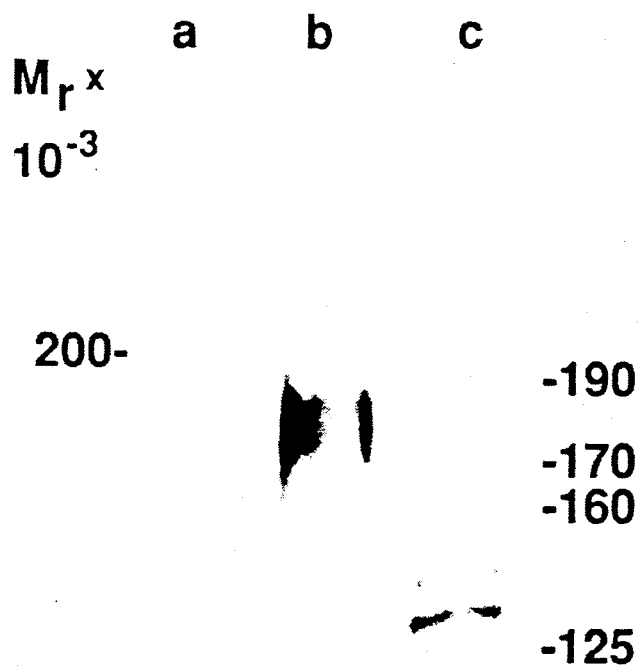

When TGF-β1-BP transfected COS cell were labeled for a shorter time (15 minutes) with $^{35}$S-methionine and $^{35}$S-cysteine, a band of 170 kDa was immunoprecipitated from the cell lysate (FIG. 6b). This band shifted to 160 kDa after degradation with endoglycosidase H, indicating that it represents a precursor form containing immature N-linked carbohydrate groups. The shift in size of the precursor after treatment with endoglycosidase H is consistent with the presence of potential N-glycosylation sites in the sequence deduced from the cDNA clone (FIG. 5c). Furthermore, the size of the deglycosylated protein (160 kDa) is close to the predicted size of the core protein (151 kDa). As expected from a mature glycoprotein, the 170–190 kDa form detected after a longer labeling time did not shift in size after endoglycosidase H treatment.

Example 8

The type III receptor for TGF-β (betaglycan) occurs in a soluble variant (Andres, et al., J. Cell. Biol. 109: 3137-3146 (1989)). Several approaches were taken to investigate the possibility that TGF-β1-BP is similar to the soluble variant of this receptor.

The type III receptor is a proteoglycan-like molecule that contain heparin sulphate and chondroitin sulphate polysaccharide chains (Cheifetz et al., supra, Segarini and Seyedin, supra). However, incubation of TGF-β1-BP immunoprecipitated from transiently expressing COS cells with heparinase, heparitinase of chondroitinase abc, did not produce any shift in mobility upon SDS-gel electrophoresis as would be expected if it had contained polysaccharide chains.

Figure 8:
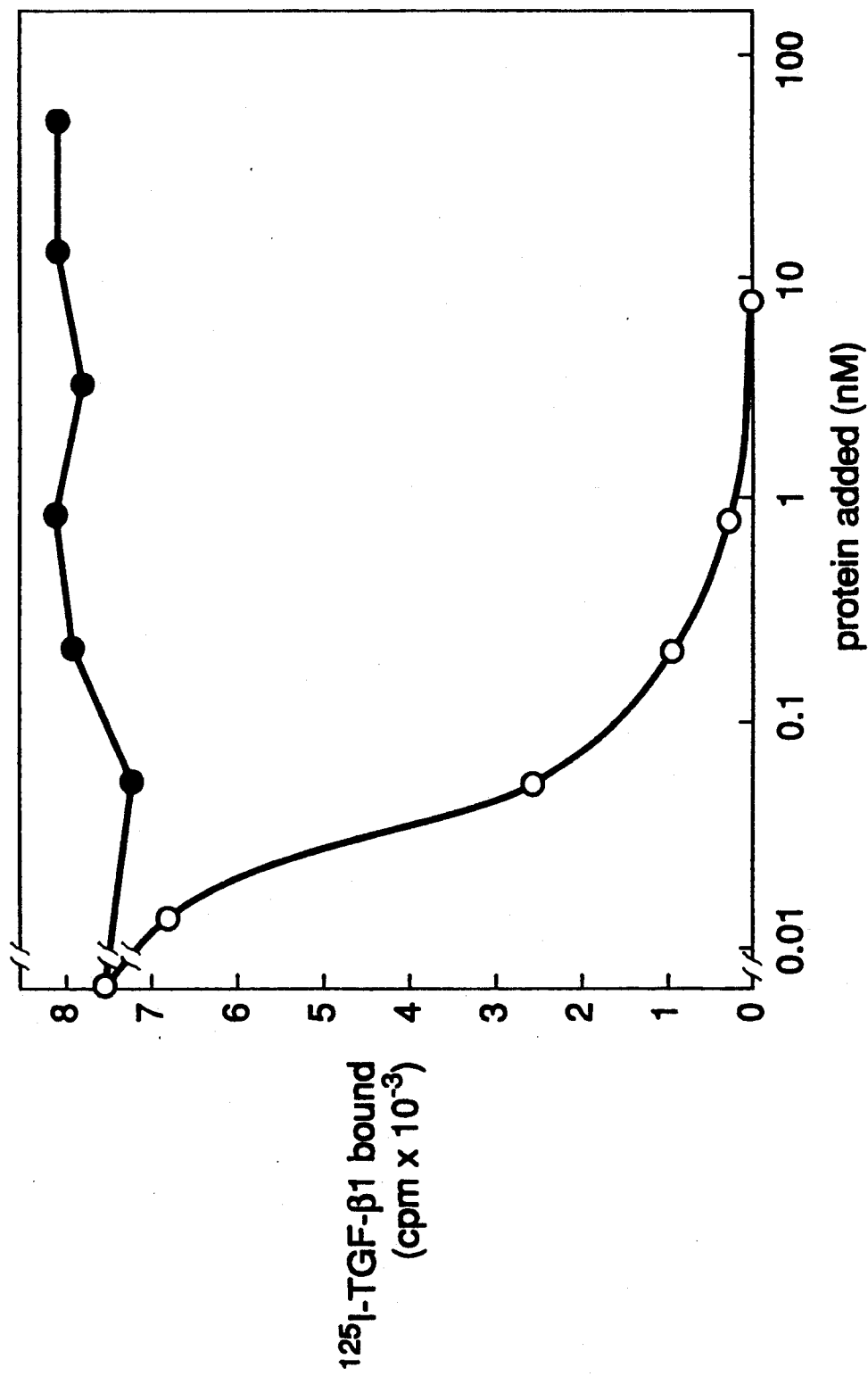
FIG. 8 shows a study of competitive binding between TGF-β1 and TGF-β1-BP to NRK cells.

In order to investigate whether TGF-β1-BP binds TGF-β1 directly, platelet TGF-β1-BP or the large latent TGF-β1 complex used as a control, were incubated with $^{125}$I-TGF-β1; after 2 hours at 4° C. a covalent cross-linker, disuccinimidyl suberate (DSS), was added. After immunoprecipitation with a TGF-β1-BP antibody, samples were analyzed by SDS-gel electrophoresis under reducing conditions and autoradiography (FIG. 7). No binding of $^{125}$I-TGF-β1 to the free form of TGF-β1-BP was recorded. In contrast, $^{125}$I-TGF-β1 was cross-linked to the large latent TGF-β1 complex; bands of 50 kDa, 90–100 kDa, 150–160 kDa and 230–260 kDa were found (FIG. 7). The sizes of these components are the expected size of $^{125}$I-TGF-β1 (12.5 kDa under reducing conditions) covalently coupled to one subunit of the N-terminal propart (40 kDa), a dimer of the propart (80 kDa), TGF-β1-BP (125–160 kDa) and all three of these components (about 210 kDa), respectively (Miyazono et al, supra). These data suggest that in the large latent TGF-β1 complex, TGF-β1-BP is located close to TGF-β1, but that TGF-β1-BP in free form has low or no affinity for TGF-β1. If TGF-β1-BP has a role in keeping TGF-β1 latent, one would expect that it would interfere with the binding of TGF-β1 to cell surface receptors. The ability of TGF-β1-BP to inhibit the binding of $^{125}$I-TGF-β1 to NRK cells was therefore investigated. As shown in FIG. 8, TGF-β1-BP had no effect on the binding of $^{125}$I-TGF-β1, even at very high concentrations. This is consistent with the conclusion that TGF-β1-BP does not bind and inactivate TGF-β1.

The foregoing experiments show that TGF-β1-BP consists mainly of two repeating sequences, i.e., the 16 EGF-like repeats, and the three repeats of a previously unknown motif. Both motifs are rich in cysteine, and the protein's most common amino acid is cysteine. The two types studied herein, i.e., platelet and fibroblast TGF-β1-BP differ markedly in size, as described supra. All of the peptides located in the platelet type protein are localized in the C-terminal 60% of the fibroblast form, suggesting that the TGF-β1-BP gene undergoes differential splicing or cells specific proteolysis.

Fibroblast TGF-β1-BP contained 15 consensus sites for beta hydroxylation of asparagine/aspartic acid. It was also shown that asparagine was beta hydroxylated at two such sites in the platelet derived protein. It is possible that the beta hydroxylation of amino acids has a role in $Ca^{2+}$ binding, although this has not yet been shown experimentally.

The binding proteins described herein also possess a so-called "RGD" sequence. These sequence are implicated in enabling proteins containing the sequence to bind to the class of cell surface molecules known as "integrins". See Hynes, Cell 48: 549–554 (1987). This suggests that the TGF-β1 binding protein may be implicated in binding to integrins in or on cell surface.

The experiments described herein suggest that the DNA for the TGF-β1-BP may also be expressed in other hematopoietic cells, the choice of which may be made by the skilled artisan.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated nucleotide sequence consisting of DNA which codes for human transforming growth factor β1 binding protein or which hybridizes to an isolated nucleotide sequence consisting of DNA which codes for human transforming growth factor β1 binding protein.

2. The isolated nucleotide sequence of claim 1, wherein said TGF-β1-BP is obtained from fibroblasts.

3. The isolated nucleotide sequence of claim 2, consisting of cDNA.

4. The isolated nucleotide sequence of claim 3, consisting of the DNA sequence depicted in FIG. 4b.

5. Vector having the isolated nucleotide sequence of claim 1 incorporated therein.

6. The isolated nucleotide sequence of claim 1, wherein said TGF-β1-BP is obtained from platelets.

7. Isolated messenger RNA consisting of an RNA sequence which expresses human transforming growth factor β1 binding protein or which hybridizes to an isolated messenger RNA consisting of an RNA sequence which expresses human transforming growth factor β1 binding protein.

8. Cell line which produces TGF-β1-BP comprising a host cell transformed with the isolated nucleotide sequence of claim 1.

9. Cell line which produces TGF-β1-BP comprising a host cell transformed with the vector of claim 5.

10. The isolated nucleotide sequence of claim 1, wherein said transforming growth factor β1 binding protein is a human protein.

11. Isolated nucleotide sequence consisting of DNA which codes for transforming growth factor β1 binding protein having amino acid sequence of FIG. 4b.

12. The isolated nucleotide sequence of claim 1, wherein said TGF-β1-BP is obtained from a hematopoietic cell.

* * * * *